United States Patent [19]

Beschke et al.

[11] 4,332,940
[45] Jun. 1, 1982

[54] PROCESS FOR THE PRODUCTION OF 2,3-CYCLOALKENOPYRIDINES

[75] Inventors: Helmut Beschke; Heinz Friedrich; Heribert Offermanns, all of Hanau, Fed. Rep. of Germany

[73] Assignee: Deutsche Gold -und Silber-Scheideanstalt Vormals Roessler, Frankfurt, Fed. Rep. of Germany

[21] Appl. No.: 830,983

[22] Filed: Sep. 6, 1977

[30] Foreign Application Priority Data

Sep. 3, 1976 [DE] Fed. Rep. of Germany ....... 2639702

[51] Int. Cl.³ .................. C07D 215/04; C07D 221/04
[52] U.S. Cl. ..................................... 546/181; 546/152; 546/112; 546/250
[58] Field of Search .................. 260/283 R, 283.54; 546/152, 181, 251, 112

[56] References Cited

U.S. PATENT DOCUMENTS

| | | | |
|---|---|---|---|
| 3,898,179 | 8/1977 | Beschke et al. | 546/251 |
| 3,917,542 | 11/1975 | Beschke et al. | 546/251 |
| 3,960,766 | 6/1976 | Beschke et al. | 546/251 |
| 4,171,444 | 10/1979 | Beschke et al. | 546/251 |
| 4,171,445 | 10/1979 | Beschke et al. | 546/251 |
| 4,175,195 | 11/1979 | Beschke et al. | 546/251 |
| 4,179,576 | 12/1979 | Miyake et al. | 546/251 |

FOREIGN PATENT DOCUMENTS 633266 12/1949 United Kingdom .

OTHER PUBLICATIONS

Breitmaier et al., "Tetrahedron Letters", No. 38 (1970), pp. 3291-3294.
Klingsberg Pyridine and Its Derivatives, Part One, Interscience, N.Y., pp. 498-500; 508 (1960).

Primary Examiner—David B. Springer
Attorney, Agent, or Firm—Cushman, Darby & Cushman

[57] ABSTRACT

2,3-Cycloalkenopyridines of the formula

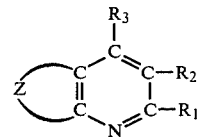

are prepared by reacting a cycloalkanone or cycloalkenone of the formula

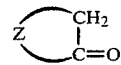

with an oxo compound of the formula

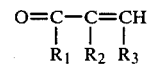

where Z is an aliphatic carbon chain which is unsubstituted or has hydrocarbon substituents and $R_1$, $R_2$ and $R_3$ are hydrogen or lower alkyl groups and ammonia in the presence of a dehydrating and dehydrogenating catalyst at a temperature of about 250° to 550° C.

23 Claims, 1 Drawing Figure

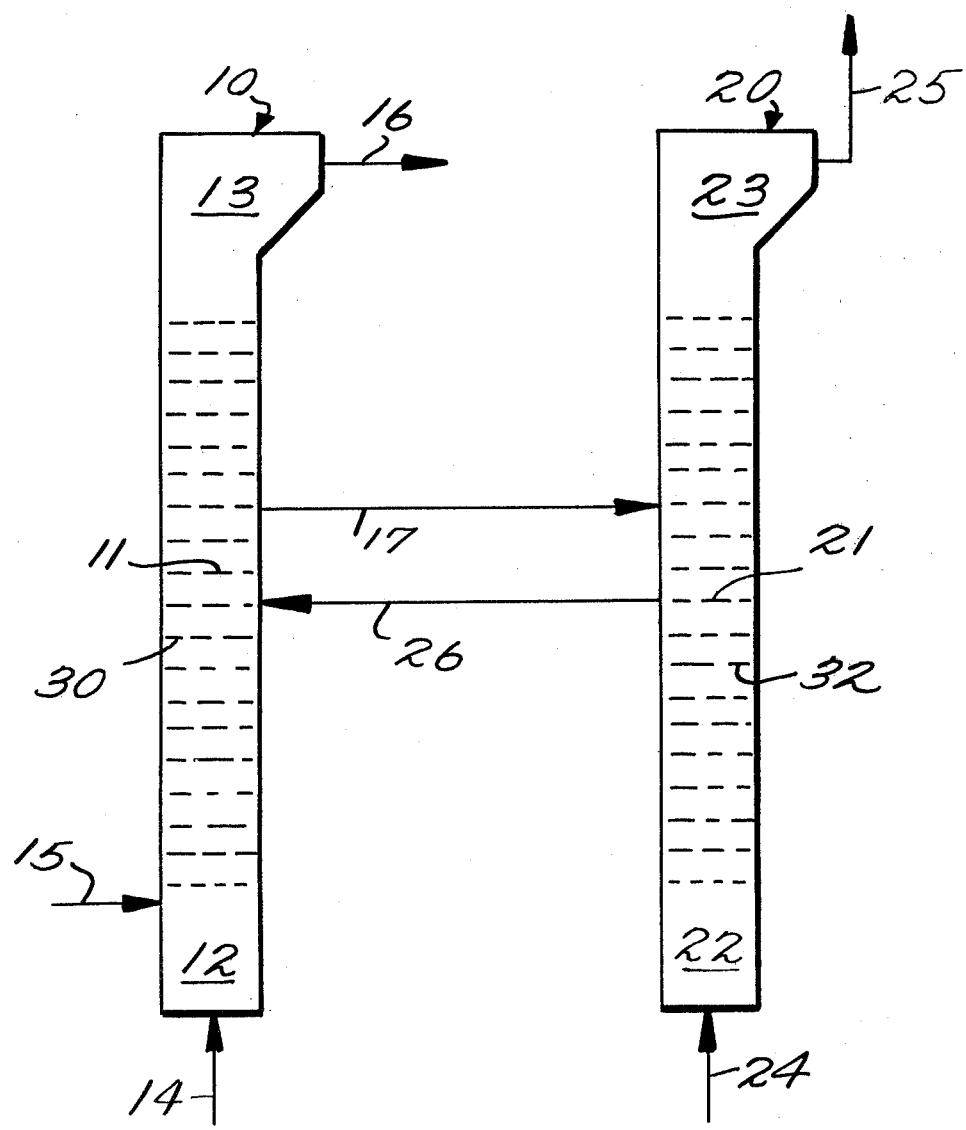

PROCESS FOR THE PRODUCTION OF 2,3-CYCLOALKENOPYRIDINES

BACKGROUND OF THE INVENTION

The invention is directed to a process for the production of 2,3-cycloalkenopyridines by the catalytic reaction of a cycloalkanone or cycloalkenone with an aliphatic oxo compound at elevated temperature. The 2,3-cycloalkenopyridines are important intermediate products for the production of medicines, plant protective agents and synthetic resins.

It is known to produce 2,3-cyclohexenopyridine by the catalytic dehydrogenation of decahydroquinoline (Berichte Vol. 67 (1934) pages 1715 to 1729). The yield is merely 36%. It is already known to produce 2,3-cyclopentenpyridine, 2,3-cyclohexenopyridine and 2,3-cycloheptenopyridine from the corresponding cycloalkanones (Annalen Vol. 478 (1939) pages 176 to 196, Helv. Chem. Acta Vol. 28 (1945) pages 1677 to 1683), in each using 4 intermediate steps. The disadvantage of these processes is that they are very expensive and the highest yield is 40%.

Furthermore, it is known to produce 2,3-cycloalkenopyridine by reaction of cycloalkanones with 3-aminoacroleins in the liquid phase at 120° C. using triethylamine and piperidine acetate as catalyst (Tetrahedron Letters No. 38 (1970) pages 3291 to 3294). This process requires as the starting materials the relatively difficulty accessible aminoacroleins. Besides despite 24 hours reaction time the yields of the desired cycloalkenopyridines are only 30 to 60%.

SUMMARY OF THE INVENTION

There has now been found a process for the production of 2,3-cycloalkenopyridines by the catalytic reaction of a cycloalkanone or cycloalkenone with an aliphatic oxo compound at elevated temperature wherein the cycloalkanone or cycloalkenone is reacted with an aliphatic oxo compound which has an unsaturated carbon to carbon double bond on the carbon atoms adjacent to the oxo group in the gas phase and with ammonia and in the presence of a dehydrating and dehydrogenating catalyst at a temperature of about 250° to 550° C. In this process the cycloalkanone or cycloalkenone is reacted with simple, easily accessible substances. High yields have been produced.

According to the invention (1) a cycloalkenone or preferably a cycloalkanone of the general formula

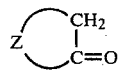 (I)

in which Z is an aliphatic carbon atom chain, preferably with 2 to 16 carbon atoms, which in a given case in branched and whose branchings in a given case are closed to a ring or several rings, or especially an aliphatic carbon chain with 3 to 10 carbon atoms, which chain may be branched, e.g., an alkylene group with or without a lower alkyl side chain, methyl being the preferred side chain is reacted (2) with an oxo compound of the general formula

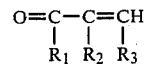 (II)

in which $R_1$, $R_2$ and $R_3$ are the same or different and are hydrogen or lower alkyl groups with preferably 1 to 6, especially 1 to 2, carbon atoms and in which in a given case the alkyl groups can be branched, and (3) with ammonia to form a compound of the general formula

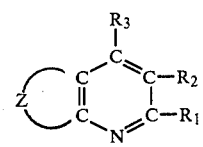 (III)

in which Z, $R_1$, $R_2$ and $R_3$ are as defined above. Z is a hydrocarbon group.

As cycloalkanones there can be used for example cyclobutanone, cyclopentadecanone, cyclohexadecanone, cyclooctadecanone, 3,5,5-trimethyl cyclohexanone, camphor, 1-decalone, 2-butyl cyclohexanone, 2-propyl cyclohexanone, 8-ketotricyclodecane, carvone, and especially cyclopentanone, cyclohexanone, cycloheptanone, cyclooctanone, cyclodecanone, cyclododecanone, 2-methyl cyclohexanone, 3-methyl cyclohexanone, 2,2,4-trimethyl cyclopentanone and menthone. An example of a cycloalkenone is isophorone.

Suitable oxo compounds are for example, methacrolein, crotonaldehyde, methyl vinyl ketone, ethyl vinyl ketone, 3-penten-2-one, hexyl vinyl ketone, heptyl vinyl ketone, 3-octene-2-one, and expecially acrolein.

The reaction conditions such as temperature and pressure and the proportions of the reacting substances and the residence time in a given case to a certain extent are dependent upon each other according to the type of reacting substances and the type of catalyst.

In general, the reaction is carried out at a temperature between 250° and 550° C. In most cases there are preferred temperatures between 300° and 500° C., especially between 350° and 450° C. It is advantageous to work at pressures of about 1 to 4 bar. However, there can also be used lower or higher pressures although it is suitable not to substantially deviate from this pressure range since it permits the use of simple apparatus.

The proportions of cycloalkanone or cycloalkenone to oxo compound (II) can be selected substantially at random, both stoichiometric as well as under or over stoichiometric being usable. Generally, it is advantageous to add about 0.5 to 10 moles of oxo compound per mole of cycloalkanone or cycloalkenone. Preferably there are used about 1 to 5 moles, especially 2 to 4 moles of oxo compound (II) per mole of cycloalkanone or cycloalkenone.

The ammonia can be present in the reaction in substantially any proportions from under stoichiometric to over stoichiometric. In most cases it is suitable to have present at least 0.5 mole of ammonia per mole of cycloalkanone or cycloalkenone, however, there can be as much as about 100 moles of ammonia per mole of cycloalkanone or cycloalkenone. Advantageously, there are employed about 1 to 20 moles of ammonia, preferably 2 to 15 moles, especially 3 to 12 moles of ammonia, per mole of cycloalkanone or cycloalkenone.

The reaction takes place in the gas phase. It can be expedient to dilute the gases of cycloalkanone or cycloalkenone, oxo compound and ammonia with inert gases. As inert gases there can be employed, for example, steam, air and especially nitrogen. Generally, it is expedient to use in all not more than about 20 moles of inert gas per mole of cycloalkanone or cycloalkenone. Preferably, there are used about 0.5 to 10 moles, particularly 1 to 5 moles of inert gas per mole of cycloalkanone or cycloalkenone.

As catalysts there can be employed those which have a dehydrating and dehydrogenating action. For example, these include the catalysts described in Hydrocarbon Processing, Vol. 47 (1968) pages 103 to 107 which are aluminum compounds such as aluminum oxide and aluminum silicate, optionally with addition of other metal oxides and fluorides. The entire disclosure of the Hydrocarbon Processing article is hereby incorporated by reference and relied upon.

With advantage there is used in the process catalysts produced according to German Offenlegungsschrift No. 2 151 417 and related Beschke U.S. Pat. No. 3,898,177; according to German OS No. 2 224 160 and related Beschke U.S. Pat. No. 3,960,766; and according to German OS No. 2 239 801 and related Beschke U.S. Pat. No. 3,917,542. The entire disclosure of Beschke Pat. Nos. 3,898,177; 3,917,542 and 3,960,766 are hereby incorporated by reference and relied upon.

These catalysts are prepared by treating with oxygen at temperatures of 550° to 1200° C. compounds of the elements Al, F and O which compounds also contain at least one element of the second, third or fourth groups of the periodic system (German Offenlegungsschrift No. 2 151 417 and related Beschke U.S. Pat. No. 3,898,177) or at least two elements of the second, fourth, fifth or sixth groups of the periodic system (German Offenlegungsschrift No. 2 224 160 and related Beschke U.S. Pat. No. 3,960,766) or at least one element of the second main group of the periodic system (German Offenlegungsschrift No. 2 239 801 and related Beschke U.S. Pat. No. 3,971,542). The catalysts are used in a fixed bed or preferably in a fluidized bed.

Beschke U.S. Pat. No. 3,898,177 describes the catalyst in claim 1 as consisting essentially of oxygen containing compounds of Al, F, at least one of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C.:

1. aluminum, aluminum oxide or an aluminum compound convertible to the oxide at said temperature;
2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate;
3. boron, silicon, boric oxide, silica or a compound of boron or silica convertible to the oxide at said temperature; and,
4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al to the total of (3) and (4) being from 1000:5 to 1000:200, the atomic ratio of the total of boron and silicon to the other element from the second and fourth groups being between 1 to 10 and 10 to 1.

Beschke U.S. Pat. No. 3,917,542 in claim 1 describes the catalyst as having been prepared by heating at 600° to 800° C. In the presence of gaseous oxygen, (1) aluminum metal, aluminum oxide or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system.

Beschke U.S. Pat. No. 3,960,766 in claim 1 describes the catalyst as consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1000 to 10 and 1000 to 800 and of Al to the elements of the second, fourth, fifth and sixth groups being between 1000 to 5 and 1000 to 2000.

Especially advantageous is a procedure using the apparatus and method of German OS No. 2 449 340 and related Beschke U.S. application Ser. No. 622,488 filed Oct. 15, 1975 in which instead of the reactants mentioned in the German OS No. 2 449 340 and Beschke cycloalkanone or cycloalkenone and oxo compound are fed into the reactor separate from the ammonia. Generally, the residence time in the reactor is between 0.2 and 5.0 seconds. The entire disclosure of the Beschke U.S. application Ser. No. 622,488 is hereby incorporated by reference and relied upon.

The working up of the gas mixture resulting from the reaction can take place in customary manner by washing the gases with a liquid, especially water or methanol and by further separation by means of extraction and distillation. With especial advantage there is employed the procedure of German OS No. 2 554 946 and related Beschke U.S. application Ser. No. 748,041 filed Dec. 6, 1976 in which the gas mixture is not washed but cooled and as a result partially condensed in such manner that any possible excess ammonia remains in the residual gas and with this is directly recycled.

BRIEF DESCRIPTION OF THE DRAWINGS

The single FIGURE of the drawing is a schematic illustration of an apparatus suitable for carrying out the invention.

Referring more specifically to the drawing, there is used a tubular reactor 10 provided with cooling and heating devices (not shown). The reactor suitably contains in the middle portion 11 gas distribution plates 30, but in the lower part 12 and the upper part 13 there is free space. The first reaction gas is led into the reactor from below through line 14 and so regulated that the catalyst in the reactor forms a fluidized bed. The other reactant gases are led through line 15 into the fluidized bed. The reaction mixture is drawn off from the reactor in the upper part thereof through the line 16. A portion of the catalyst is always transported via line 17 from the reactor 10 to a regenerator 20. This regenerator also is advantageously constructed similar to the reactor 10. The regenerator also suitably contains gas distribution plates 32 in the middle portion but there is free space in the lower portion 22 and in the upper portion 23. The oxygen or oxygen containing gas is led into the regenerator 20 from below through line 24. The gas flow is so regulated that the catalyst present in the regenerator forms a fluidized bed. The gas escaping from the regenerator via line 25 is discarded. A portion of the catalyst is continuously relieved from the regenerator 20 via line 26 into the reactor 10.

Unless otherwise indicated all parts and percentages are by weight.

The process can comprise, consist essentially of or consist of the steps set forth and the materials can comprise, consist essentially of or consist of those set forth.

DESCRIPTION OF THE PREFERRED EMBODIMENTS

Example 1

There was used the apparatus of the drawing (also disclosed in German OS No. 2 449 340 and Beschke U.S. application Ser. No. 622,488). Reactor 10 and regenerator 20 consisted of tubes 70 mm wide which had in their lower portions a free space 12 or 22 which was 200 mm high; thereover at intervals of 50 mm there were provided 40 wire screens with meshes of 5 mm (30 and 32) each in the spaces 11 and 21. There were provided above free spaces 13 and 23 having a height of 600 mm and a width of up to 160 mm.

There were led into the reactor 10 in gaseous form in uniform flow hourly from below via line 14 a gas mixture of 1500 normal liters (i.e., measured at standard pressure and temperature) of nitrogen and 2150 normal liters of ammonia. In a vaporizer there was prepared hourly a gas mixture from 2130 grams of acrolein and 325 normal liters of nitrogen. In a further vaporizer there was prepared a similar gaseous mixture from 1820 grams of cyclododecanone and 325 normal liters of nitrogen. These gaseous mixtures were combined and from the side via line 15 were led into the fluidized layer 130 mm above the bottom of the reactor at a temperature of 250° C.

The reactor contained 2.0 kg of catalyst which was produced according to Beschke U.S. Pat. No. 3,960,766 Example 1a (and German Offenlegungsschrift No. 2 224 160) from aluminum oxide, magnesium nitrate and titanium tetrafluoride and had an atomic ratio of aluminum to magnesium to titanium to fluorine of 1000:25:25:100. The catalyst had a particle size between 0.4 and 1.0 mm. The temperature in the reactor was held at 440° C. The reaction mixture leaving via line 16 and which was free from acrolein and cyclododecanone was led at a temperature of 250° C. into a gas washing apparatus in which the 2,3-cyclododecenopyridine and the pyridine and 3-methyl pyridine byproducts were washed out by means of methanol. The remaining residual gas of ammonia and nitrogen was recycled into the reactor.

The regenerator 20 contained an additional 2.0 kg of the catalyst. There were introduced into the regenerator from below via line 24 hourly 3000 normal liters of air. The temperature in the regenerator was held at 440° C. In a steady stream there were transferred hourly from the reactor to the regenerator 1.4 kg of catalyst and likewise there were returned 1.4 kg of catalyst from the regenerator to the reactor.

The cyclododecanone reaction was 98%. There were recovered hourly 1895 grams of 2,3-cyclododecenopyridine, 378 grams of pyridine and 1164 grams of 3-methyl pyridine as well as 25 grams of unreacted cyclododecanone. This corresponds to a yield of cyclododecenopyridine of 88.6%, based on the reacted cyclododecanone as well as 12.5% of pyridine and 32.9% of 3-methyl pyridine based on the acrolein added. The 2,3-cyclododecenopyridine had a boiling point of 141° to 144° C. at 5 mbar. Its hydrochloride had a melting point (decomposition point) of 220° C.

In the following examples, there was used the same procedure as in Example 1.

Example 2

| | |
|---|---|
| Starting Materials: | Cycloheptanone, acrolein and ammonia in the molar ratios of 1:2.8:11.2 |
| Catalyst: | As in Example 1 |
| Reaction Temperature: | 430° C. |
| Reaction: | 100% of the cycloheptanone |
| Product: | 2,3-cycloheptenopyridine B.P. 104 to 114° C. at 17 mbar, M.P. of the hydrochloride 158° C. |
| Yield: | 69% based on the reacted cycloheptanone |
| Byproducts: | 11% pyridine and 30% 3-methyl pyridine based on the acrolein added |

Example 3

| | |
|---|---|
| Starting Materials: | Cyclopentanone, acrolein and ammonia in the molar ratios of 1:2.8:11.2 |
| Catalyst: | As in Example 1 |
| Reaction Temperature: | 420° C. |
| Reaction: | 100% of the cyclopentanone |
| Product: | 2,3-cyclopentenopyridine, B.P. 78 to 83° C. at 17 mbar, M.P. (decomposition point) of the hydrochloride 153° C. |
| Yield: | 64% based on the reacted cyclopentanone |
| Byproducts: | 12% pyridine and 31% 3-methyl pyridine based on the acrolein added |

EXAMPLE 4

| | |
|---|---|
| Starting Materials: | 3-methyl-5-dimethylcyclohexanone, acrolein and ammonia in the molar ratios of 1:3:12 |
| Catalyst: | As in Example 1 |
| Reaction Temperature: | 440° C. |
| Reaction: | 100% of the 3-methyl-5-dimethylcyclohexanone |
| Product: | Isomeric mixture of 60% 5-methyl-7-dimethyl-5,6,7,8-tetrahydroquinoline and 40% 5-dimethyl-7-methyl-5,6,7,8-tetrahydroquinoline B.P. 115 to 120° C. at 17 mbar |
| Yield: | A total of 71% based on the reacted cyclohexanone |
| Byproducts: | 12% pyridine and 29% 3-methyl pyridine based on the acrolein added |

Example 5

| | |
|---|---|
| Starting Materials: | Cyclohexanone, acrolein and ammonia in the molar ratios of 1:2.9:9.6 |
| Catalyst: | According to Beschke U.S. Pat. No. 3,898,177 Example 5 (and German OS 2 151 417) from aluminum oxide, magnesium nitrate and fluosilicic acid, atomic ratio aluminum to magnesium to silicon to fluorine of 1000:24:25:156 |
| Reaction Temperature: | 400° C. |
| Reaction: | 94% of the cyclohexanone |
| Product: | 2,3-cyclohexenopyridine, B.P. 95 to 99° C. at 17 mbar, M.P. of the hydrochloride 134° C. |
| Yield: | 53% based on the reacted cyclohexanone |
| Byproducts: | 15% pyridine and 25% 3-methyl pyridine based on the acrolein added |

Example 6

| | |
|---|---|
| Starting Materials: | Cyclohexanone, acrolein and ammonia in the molar ratios of 1:2.4:6 |
| Catalyst: | According to Beschke U.S. Pat. No. 3,917,542 Example 1 (and German OS 2 239 801) from aluminum oxide, magnesium nitrate and ammonium hydrogen fluoride in the atomic ratio aluminum to magnesium to fluorine of 1000:25:50 |
| Reaction Temperature: | 370° C. |
| Reaction: | 92% of the cyclohexanone |
| Product: | 2,3-cyclohexenopyridine, B.P. 95 to 99° C. at 17 mbar, M.P. of the hydrochloride 134° C. |
| Yield: | 58% based on the reacted cyclohexanone |
| Byproducts: | 14% pyridine and 21% 3-methyl pyridine based on the acrolein added |

Example 7

| | |
|---|---|
| Starting Materials: | Cyclododecanone, crotonaldehyde and ammonia in the molar ratios of 1:2:8 |
| Catalyst: | As in Example 1 |
| Reaction Temperature: | 430° C. |
| Reaction: | 100% of the cyclododecanone |
| Product: | 2,3-cyclododeceno-4-methyl pyridine, B.P. 172 to 183° C. at 6 mbar |
| Yield: | 37% based on the reacted cyclododecanone |
| Byproducts: | 8% pyridine, 11% 2-methyl pyridine and 21% 4-methyl pyridine based on the crotonaldehyde added |

Example 8

| | |
|---|---|
| Starting Materials: | Cyclohexanone, methacrolein and ammonia in the molar ratios of 1:3:6 |
| Catalyst: | As in Example 1 |
| Reaction Temperature: | 420° C. |
| Reaction: | 100% of the cyclohexanone |
| Product: | 2,3-cyclohexeno-5-methyl pyridine, B.P. 96 to 102° C. at 13 mbar |
| Yield: | 64% based on the reacted cyclohexanone |
| Byproducts: | 5% pyridine and 27% 3,5-dimethyl pyridine based on the methacrolein added |

Example 9

| | |
|---|---|
| Starting Materials: | Cyclododecanone, methyl vinyl ketone and ammonia in the molar ratios 1:2.6:10.4 |
| Catalyst: | As in Example 1 |
| Reaction Temperature: | 420° C. |
| Reaction: | 100% of the cyclododecanone |
| Product: | 2,3-cyclododeceno-6-methyl pyridine, B.P. 146 to 158° C. at 3 mbar |
| Yield: | 73% based on the reacted cyclododecanone |
| Byproducts: | 27% collidine mixture based on the methyl vinyl ketone added |

Example 10

| | |
|---|---|
| Starting Materials: | Cyclohexanone, acrolein and ammonia in the molar ratio 1:1:4 |
| Catalyst: | Aluminum silicate consisting of 87% $SiO_2$ and 13% $Al_2O_3$, BET surface area 500 m$^2$/g, particle size 0.4 to 1.0 mm, pore volume 0.75 cm$^3$/g, pore diameter 60 angstroms |
| Reaction Temperature: | 440° C. |
| Reaction: | 100% of the cyclohexanone |
| Product: | 2,3-cyclohexenopyridine, B.P. 95 to 99° C. at 17 mbar, M.P. of the hydrochloride 134° C. |
| Yield: | 38% based on the reacted cyclohexanone |
| Byproducts: | 13% pyridine and 34% 3-methyl pyridine based on the acrolein added |

Example 11

| | |
|---|---|
| Starting Materials: | 2,2,4(2,4,4)-trimethylcyclopentanone (TMCP-on of the firm VEBA), acrolein and ammonia in the molar ratios 1:3:12 |
| Catalyst: | As in Example 1 |
| Reaction Temperature: | 420° C. |
| Reaction: | 100% of the trimethylcyclopentanone |
| Product: | Mixture of 1'-dimethyl-3'-methyl-2,3-cyclopentenopyridine and 1'-methyl-3'-dimethyl-2,3-cyclopentenopyridine, B.P. 88 to 103° C. at 14 mbar |
| Yield: | 37% based on the reacted trimethylcyclopentanone |
| Byproducts: | 31% pyridine and 36% 3-methylpyridine based on the acrolein added |

EXAMPLE 12

| | |
|---|---|
| Starting Materials: | Isophorone (3,5,5-trimethyl-2-cyclohexenone), acrolein and |

| | |
|---|---|
| | ammonia in the molar ratios of 1:3:10 |
| Catalyst: | As in Example 1 |
| Reaction Temperature: | 420° C. |
| Reaction: | 94% of the isophorone |
| Product: | (a) 5-dimethyl-7-methyl-5,6-dihydroquinoline |
| | (b) 5-dimethyl-7-methyl-5,6,7,8-tetrahydroquinoline |
| | (c) 5,7-dimethyl quinoline |
| Yield: | 55% ((a) 5%, (b) 16%, (c) 34%) based on the reacted isophorone |
| Byproducts: | 16% pyridine and 30% 3-methyl pyridine based on the acrolein added |

What is claimed is:

1. In a process for the production of a 2,3-cycloalkenopyridine of the formula

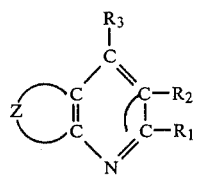   III where Z is an unsubstituted or 1 to 6 carbon atoms alkyl substituted aliphatic carbon chain having a 2 to 16 carbon atoms and $R_1$, $R_2$ and $R_3$ are hydrogen or 1 to 6 carbon atom alkyl group comprising the step of catalytically reacting a cycloalkanone of the formula

   I or isophorone with an oxo compound having the formula

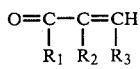   II and ammonia in the gas phase at a temperature from about 250° to 550° C., the improvement comprising carrying out the reaction in the presence of a dehydrating and dehydrogenating catalyst which is (1) a catalyst consisting essentially of oxygen containing compounds of Al, F at least one of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C.;
 1. aluminum, aluminum oxide or an aluminum compound convertible to the oxide at a said temperature,
 2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate,
 3. boron, silicon, boric oxide, silica or a compound of boron or silica convertible to the oxide at said temperature and
 4. magnesium, zinc, tin, zirconium, magnesium oxide, zinc oxide, tin oxide or a compound of zirconium or barium convertible to the oxide at said temperature, the atomic ratio of Al to F being from 1000:25 of 1000:800 and the atomic ratio of Al to the total of (3) and (4) being from 1000:5 to 1000:200, the atomic ratio of the total of boron and silicon to the other element from the second and fourth groups being between 1 to 10 and 10 to 1 or (2) a catalyst having been prepared by heating at 600° to 800° C. in the presence of gaseous oxygen (1) aluminum metal, aluminum oxide, or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system or (3) a catalyst consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1,000 to 10 and 1,000 to 800 and of Al to the elements of the second, fourth, fifth and sixth groups being between 1,000 to 5 and 1,000 to 200.

2. The process according to claim 1 wherein Z is unsubstituted or has 1 to 3 methyl substituents.

3. The process of claim 2 wherein $R_1$, $R_2$ and $R_3$ are hydrogen or alkyl of 1 to 2 carbon atoms.

4. The process of claim 3 wherein (II) is acrolein.

5. The process of claim 1 wherein (I) is an unsubstituted cycloalkanone of 4 to 18 carbon atoms, trimethylcyclohexanone, 8-ketotricyclodecane, carvone, methyl cyclohexanone, trimethylcyclopentanone, isophorone or menthone and (II) is acrolein, methacrolein, crotonaldehyde, alkyl vinyl ketone having 1 to 2 carbon atoms in the alkyl group and 3-penten-2-one.

6. The process of claim 5 wherein (I) is cyclododecanone, cycloheptanone, cyclopentanone, 3-methyl-5-dimethyl-2-cyclohexanone, cyclohexanone, 2,2,4-trimethylcyclopentanone or isophorone and (II) is acrolein, methacrolein, crotonaldehyde or methyl vinyl ketone.

7. The process of claim 6 wherein (II) is acrolein.

8. The process of claim 5 wherein (I) is an unsubstituted cycloalkanone of 5 to 12 carbon atoms or 3-methyl-5-dimethylcyclohexanone and (II) is acrolein, methacrolein or methyl vinyl ketone.

9. The process of claim 1 wherein the reaction temperature is 300° to 500° C.

10. The process of claim 9 wherein the reaction temperature is 350° to 450° C.

11. The process of claim 9 wherein the catalyst is (1).

12. The process of claim 1 wherein there is used 1 to 5 moles of oxo compound per mole of cycloalkanone or isophorone.

13. The process of claim 12 wherein there is used 1 to 20 moles of ammonia per mole of cycloalkanone or isophorone.

14. The process of claim 13 wherein the reaction is carried out in the presence of an inert gas.

15. The process of claim 14 comprising carrying out the reaction in a fluidized bed and the cycloalkanone or isophorone and oxo compound are added together to the reaction zone separate from the ammonia.

16. The process of claim 1 wherein there is used 0.5 to 10 moles of oxo compound per mole of cycloalkanone or isophorone.

17. The process of claim 16 wherein there is employed 0.5 to 100 moles of ammonia per mole of cycloalkanone or isophorone.

18. The process of claim 17 wherein there is employed 3 to 12 moles of ammonia and 1 to 5 moles of oxo compound per mole of cycloalkanone or isophorone.

19. The process of claim 18 wherein there is used 4 to 12 moles of ammonia per mole of cycloalkanone or isophorone.

20. The process of claim 17 wherein there is used 1 to 10 moles of oxo compound and 4 to 100 per mole of cycloalkanone or isophorone.

21. The process of claim 1 wherein the catalyst is catalyst (1).

22. The process of claim 1 wherein the catalyst is catalyst (2).

23. The process of claim 1 wherein the catalyst is catalyst (3).

* * * * *